(12) United States Patent
Rezach

(10) Patent No.: US 10,772,662 B2
(45) Date of Patent: Sep. 15, 2020

(54) SURGICAL INSTRUMENT AND METHOD

(71) Applicant: Warsaw Orthopedic, Inc., Warsaw, IN (US)

(72) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 889 days.

(21) Appl. No.: 14/522,281

(22) Filed: Oct. 23, 2014

(65) Prior Publication Data

US 2016/0113694 A1    Apr. 28, 2016

(51) Int. Cl.
*A61B 17/70* (2006.01)

(52) U.S. Cl.
CPC ........ *A61B 17/7077* (2013.01); *A61B 17/708* (2013.01); *A61B 17/7079* (2013.01)

(58) Field of Classification Search
CPC ............ A61B 17/7077; A61B 17/7079; A61B 17/708
USPC ........................................ 606/246–279, 86 A
See application file for complete search history.

(56) References Cited

U.S. PATENT DOCUMENTS

| | | | |
|---|---|---|---|
| 2004/0267266 A1* | 12/2004 | Daniels | A61B 17/162 606/80 |
| 2009/0204159 A1* | 8/2009 | Justis | A61B 17/708 606/323 |

\* cited by examiner

*Primary Examiner* — Si Ming Ku

(74) *Attorney, Agent, or Firm* — Sorell, Lenna & Schmidt, LLP

(57) ABSTRACT

A surgical connector is provided. The connector includes a first member including a mating surface engageable with an implant and a locking element and a second member translatable relative to the first member to urge the locking element into engagement with the implant. At least one of the members is connectable with a surgical instrument. Systems and methods of use are disclosed.

20 Claims, 6 Drawing Sheets

SURGICAL INSTRUMENT AND METHOD

TECHNICAL FIELD

The present disclosure generally relates to medical devices for the treatment of musculoskeletal disorders, and more particularly to a surgical system and a method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments may employ implants that are manipulated for engagement with vertebrae to position and align one or more vertebrae. In some embodiments, the implants can include bone fasteners that are manipulated with surgical instruments for positioning and alignment of vertebrae. This disclosure describes an improvement over these prior art technologies.

SUMMARY

A surgical connector is provided. The surgical connector comprises a first member that includes a mating surface engageable with an implant and a locking element. A second member is translatable relative to the first member to urge the locking element into engagement with the implant. At least one of the members is connectable with a surgical instrument. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
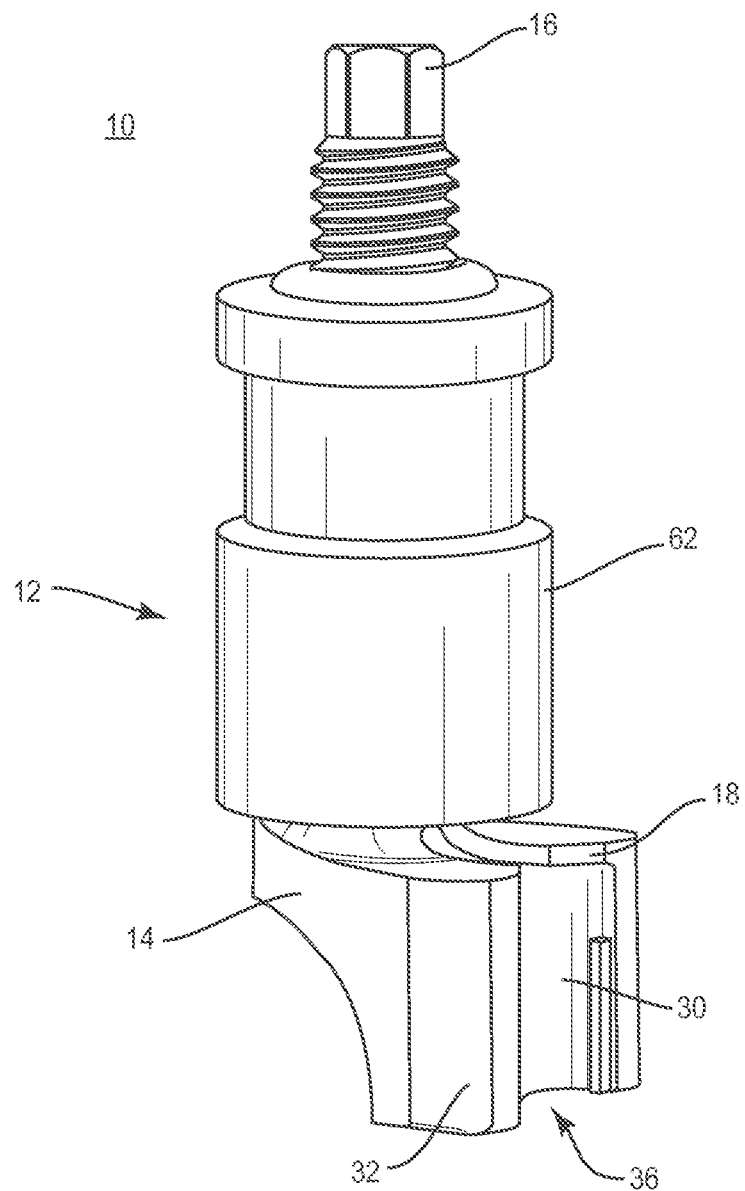
FIG. 1 is a perspective view of components of one embodiment of a system in accordance with the principles of the present disclosure.

The exemplary embodiments of a surgical system are discussed in terms of medical devices for the treatment of musculoskeletal disorders and more particularly, in terms of a surgical system and a method for correction of a spine disorder. In some embodiments, the present disclosure provides a surgical system for delivering and/or fastening implants with a surgical site and a method for treating a spine. In one embodiment, the present system includes a connector, such as, for example, an adapter that connects an instrument with a spinal implant, such as, for example, a bone fastener. In one embodiment, the connector comprises a rigid instrument implant interface.

In one embodiment, the adapter is configured to translate over the bone fastener. In some embodiments, this configuration allows a surgical instrument to slide down over the bone screw. In one embodiment, the adapter is configured to form a rigid connection with the bone fastener. In one embodiment, a rigid attachment is created with the bone fastener such that the adapter has a tapered surface that engages the bone fastener to push a spring finger toward the bone fastener to facilitate engagement. In some embodiments, the adapter is configured for connecting one or a plurality of surgical instruments to an implant. In some embodiments, the adapter is monolithically formed with an extender and/or a reducer.

In some embodiments, the system includes an adapter that creates a robust, toggle free interface between an implant and a surgical instrument. In some embodiments, the adapter connects a surgical instrument with one or more spinal implants, such as, for example, multi-axial screws (MAS), fixed axis screws (FAS) or pedide screws. In some embodiments, the adapter connects a surgical instrument with a bone screw having a receiver with axial slots disposed alongside an implant cavity configured to receive a spinal rod.

In one embodiment, the adapter includes a member having a bent spring finger and a sleeve. In one embodiment, the member comprises a surface having a conical surface configured to facilitate translation of the spring finger. In one embodiment, the sleeve is configured to slide over the member to contact and push the bent spring finger to a dosed position. In one embodiment, a nut is translated along a threaded surface on the member to push the sleeve along the member.

In some embodiments, the system can be employed with a method for treating a spine disorder, such as, for example, trauma and/or a procedure for correction of one or more osteotomized vertebra. In one embodiment, the method includes the step of translating or sliding an adapter onto an implant. In one embodiment, the method includes the step of bottoming out the adapter against a proximal surface of the implant. In one embodiment, the method includes the step of securing a nut with a member of the adapter to secure the adapter to the implant.

In some embodiments, the system of the present disclosure may be employed to treat spinal disorders, such as, for example, degenerative disc disease, disc hemiation, osteoporosis, spondylolisthesis, stenosis, scoliosis and other curvature abnormalities, kyphosis, tumor and fractures. In some embodiments, the system of the present disdosure may be employed with other osteal and bone related applications, induding those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context dearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system 10.

The components of system 10 can be fabricated from biologically acceptable materials suitable for medical applications, including metals, synthetic polymers, ceramics and/or their composites. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof, thermoplastics such as polyaryletherketone (PAEK) induding polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes a connector, such as, for example, an adapter 12 that connects a surgical instrument (not shown), as described herein, with a spinal implant, such as, for example, a bone fastener 100 (FIGS. 6 and 7) to correct a spinal disorder, such as, for example, trauma and/or fracture of vertebrae, which may include a sagittal deformity, as described herein.

Adapter 12 includes a member, such as, for example, a post 14. Post 14 extends between an end 16 and an end 18. In one embodiment, all or only a portion of post 14 comprises a substantially cylindrical cross-section. In some embodiments, the cross-section of post 14 may be oval, rectangular, polygonal, irregular, tapered, offset, staggered, uniform and/or non-uniform.

End 16 includes a threaded surface 56. Surface 56 is configured for engagement with an actuator 80 (FIG. 6) such that actuator 80 drives a member, such as, for example, a collar 62 relative to post 14, as described herein. Surface 56 extends along at least a portion of end 16. In some embodiments, the thread form on surface 56 may include a single thread turn or a plurality of discrete threads. In one embodiment, end 16 includes a tool engagement surface 58. In one embodiment, surface 58 has a hexagonal cross-section to facilitate engagement with a surgical instrument or tool. In some embodiments, surface 58 may have alternative cross-sections, such as, for example, rectangular, polygonal, hexalobe, oval, or irregular. In one embodiment, surface 58 may have alternate surface configurations, such as, for example, rough, arcuate, undulating, mesh, porous, semi-porous, dimpled and/or textured.

Post 14 includes a pair of spaced arms 30 and 32 disposed adjacent end 18. Arm 30 includes an inner surface 31, and arm 32 includes an inner surface 33. Surfaces 31, 33 extend to form a mating surface 34. Surface 34 has a concave configuration forming an implant cavity 36 to facilitate engagement with an implant, such as, for example, bone fastener 100. In some embodiments, surface 34 may have other configurations, such as, for example, semi-circular, partially cylindrical, oval, rectangular, polygonal, irregular, tapered, staggered, uniform and non-uniform.

Mating surface 34 includes a flange 38 engageable with a recess of an outer surface of an implant, such as, for example, bone fastener 100. In one embodiment, mating surface 34 includes two, opposing flanges; a flange 38 disposed with arm 30 and a flange 38 disposed with arm 32. The opposing flanges 38 mate with and engage corresponding aligned recesses of a receiver of bone fastener 100, as described herein. Mating surface 34 defines stop limits 40, 42 that extend into cavity 36. Limits 40, 42 provide a stop feature limiting translation bone fastener 100 within cavity 36 relative to adapter 12. In some embodiments, mating surface 34 may include one or a plurality of flanges.

Figure 5:
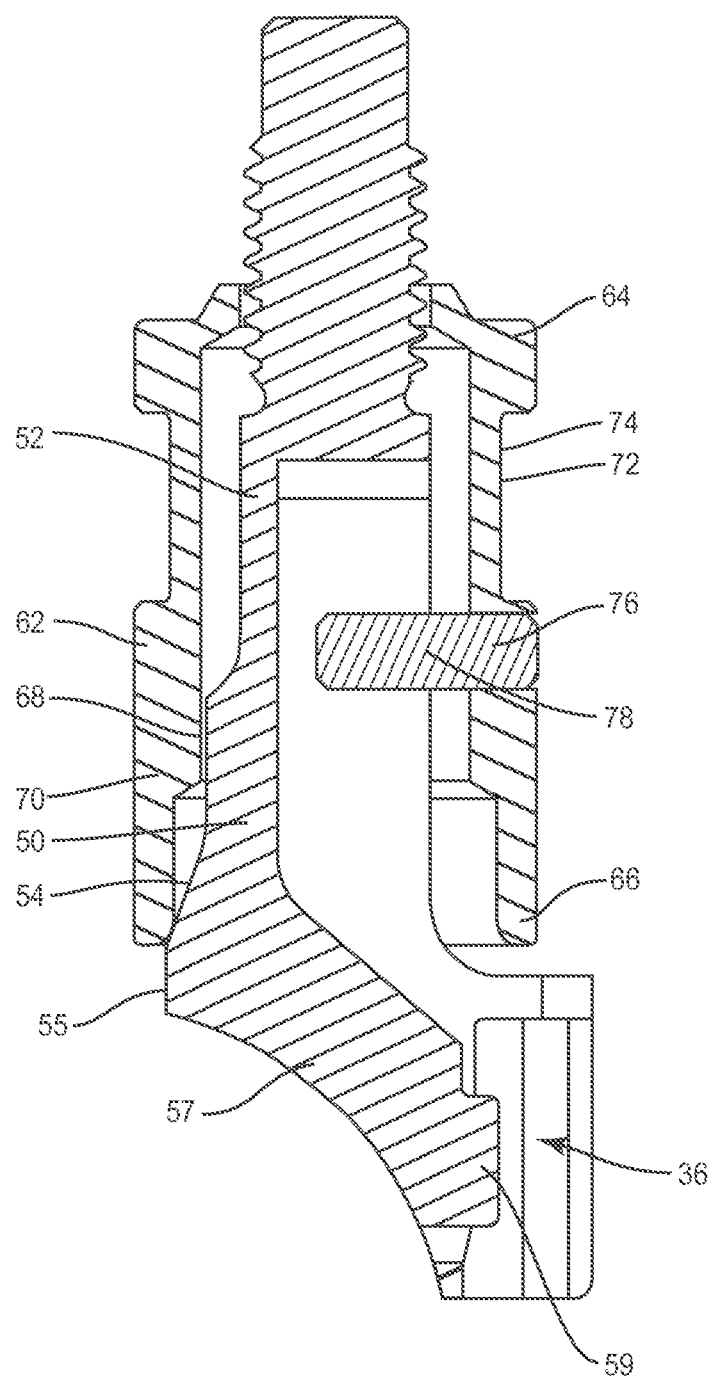
FIG. 5 is a side cross-section view of the components shown in FIG. 1.
Figure 8:
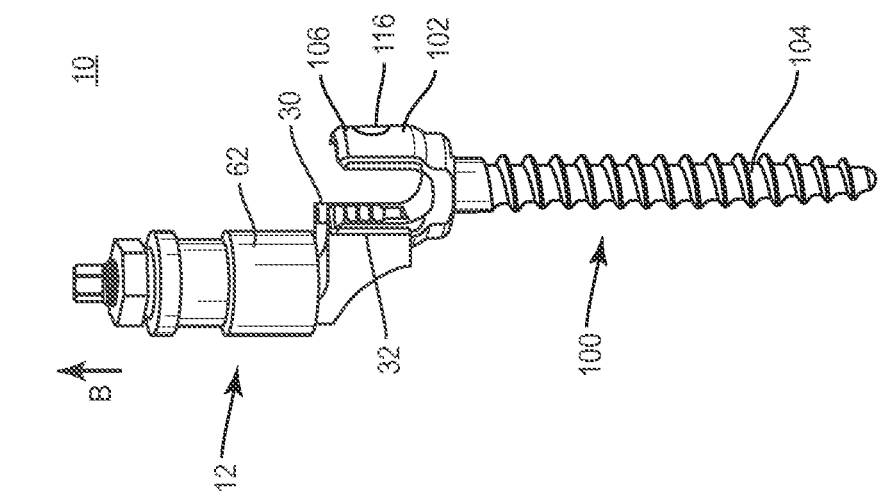
FIG. 8 is a perspective view of the components shown in FIG. 7.

Post 14 includes a locking element, such as, for example, an extension 50 configured to lock bone fastener 100 relative to adapter 12. Extension 50 extends distally from end 16 along a portion of post 14 such that extension 50 is disposed in cavity 36. In one embodiment, extension 50 is attached to post 14 via connection point 52 adjacent end 16. In one embodiment, extension 50 flexibly extends from connection point 52, such that extension 50 is resiliently biased to a selected position, as described herein. Extension 50 includes a surface 54, as shown in FIG. 5, configured for engagement with an inner surface of a collar 62, as described herein. Surface 54 includes a conical surface having a ledge 55. Engagement of surface 54 with collar 62 causes extension 50 to move, pivot and/or rotate about connection point 52 between a position such that extension 50 is aligned with mating surface 34, as shown in FIGS. 2 and 7, and a position such that extension 50 engages an implant, such as, for example, bone fastener 100, as shown in FIGS. 5 and 8.

Extension 50 includes a surface 57, as shown in FIG. 5, configured to engage an implant, such as, for example, bone fastener 100. Surface 57 defines a locking surface, such as, for example, a tab 59. Tab 59 is positioned adjacent a distal end of extension 50 and extends transversely from extension 50 into cavity 36. In one embodiment, tab 59 has a cylindrical shape. In some embodiments, tab 59 may include alternate shapes, such as, for example, round, partially cylindrical, oval, rectangular, polygonal, irregular, tapered, offset, staggered, uniform and non-uniform. In some embodiments, tab 59 may extend in alternate orientations, such as, for example, angled, offset and/or staggered.

Figure 2:
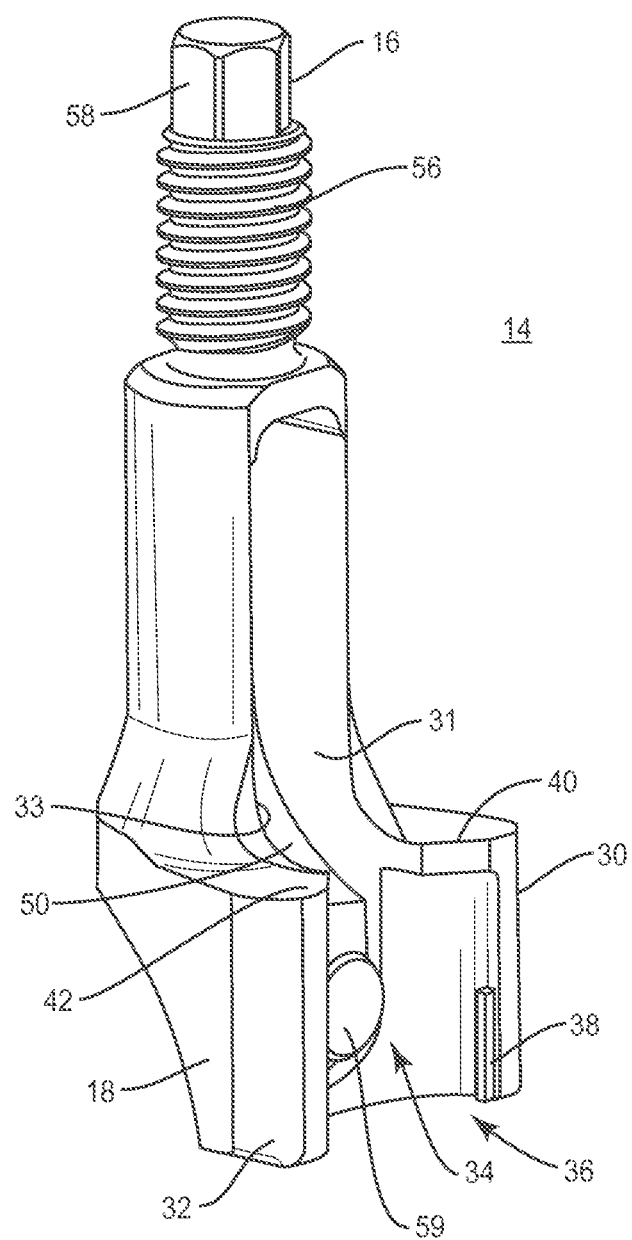
FIG. 2 is a perspective view of components of the system shown in FIG. 1.
Figure 3:
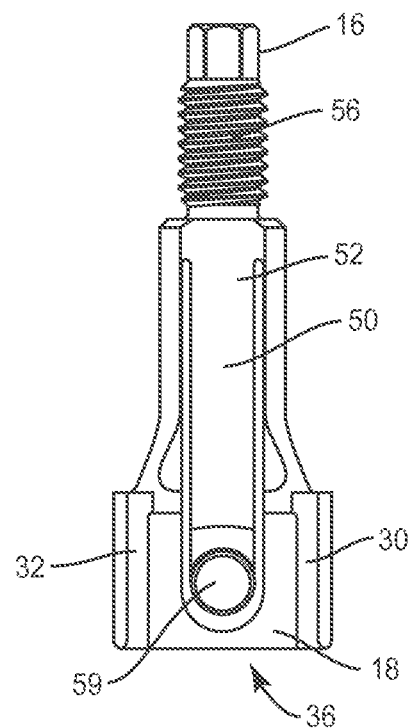
FIG. 3 is a side view of the components shown in FIG. 2.
Figure 4:
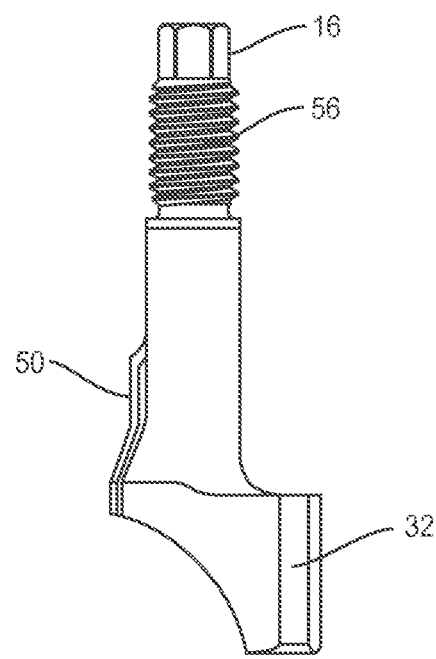
FIG. 4 is a side view of the components shown in FIG. 2.
Figure 7:
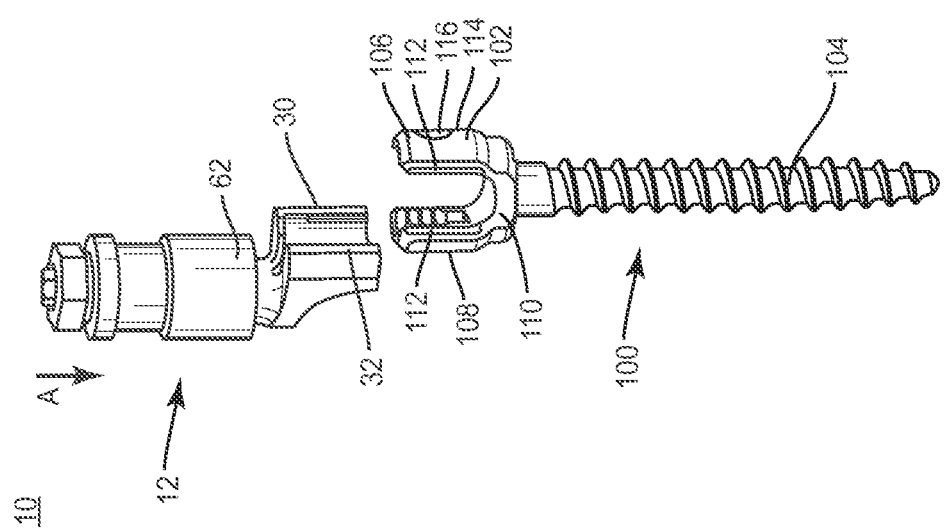
FIG. 7 is a perspective view of components of one embodiment of a system in accordance with the principles of the present disclosure.

For example, in a selected position, as shown in FIGS. 2 and 7 and described herein, surface 56 is disposed in a flush and/or even alignment with mating surface 34. In some embodiments, in a selected position, as shown in FIGS. 2 and 7 and described herein, tab 59 is disposed in a flush and/or even alignment with mating surface 34. Movement of extension 50 causes tab 59 to move, pivot and/or rotate about connection point 52 for mating engagement with a correspondingly configured recess of an outer surface of an implant, such as, for example, bone fastener 100, as shown in FIGS. 5 and 8.

In some embodiments, extension 50 is movable between selected positions such that extension 50 and/or tab 59 are aligned with mating surface 34 and pivotable such that tab 59 is biased into cavity 36 via engagement with collar 62 into a recess of bone fastener 100 for capture thereof. In one embodiment, extension 50 can be resiliently biased to a first position and urged via collar 62 into a second position. For example, extension 50 can be biased such that tab 59 is aligned with mating surface 34 and movable to the second position in which tab 59 is biased into cavity 36. In one embodiment, surfaces 54, 56 may have alternate surface configurations, such as, for example, rough, arcuate, undulating, mesh, porous, semi-porous, dimpled and/or textured.

Collar 62 is configured for translation along post 14 to urge extension 50 into engagement with bone fastener 100. Collar 62 comprises a sleeve having a cylindrical cross-section that is disposed about post 14. Collar 62 extends between an end 64 and an end 66. In some embodiments, the cross-section of collar 62 may be round, partially cylindrical, oval, rectangular, polygonal, irregular, tapered, offset, staggered, uniform and non-uniform.

Collar 62 includes an inner surface 68 that extends along the length of collar 62. Surface 68 includes a tapered portion that includes a ledge 70 configured for engagement with ledge 55 to move extension 50 into engagement with bone fastener 100. Surface 68 may have alternate surface configurations, such as, for example, rough, arcuate, undulating, mesh, porous, semi-porous, dimpled and/or textured. Collar 62 includes an outer surface 72. In some embodiments, surface 72 includes a recessed portion 74 configured to facilitate engagement with a surgical instrument and/or tool. In some embodiments, surface 68 defines an annular ledge 76 configured to engage surfaces 31, 33 to resist and/or prevent post 14 from rotating when engaged with bone fastener 100. Ledge 76 includes surface 78 configured for contact with surfaces 31, 33.

Figure 6:
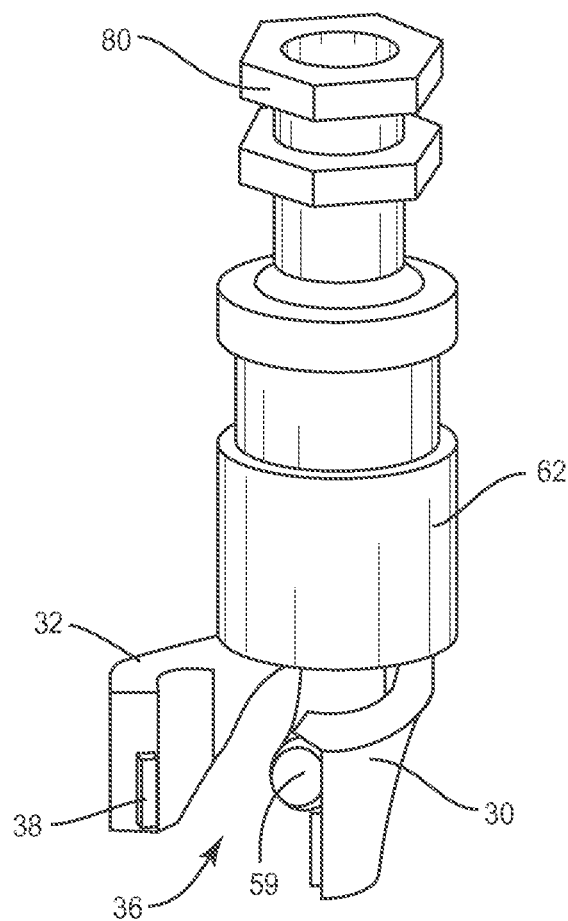
FIG. 6 is a perspective view of components of one embodiment of a system in accordance with the principles of the present disclosure.

An actuator 80, as shown in FIG. 6, is threaded with surface 56 for axial translation relative thereto. Actuator 80 is configured to abut and engage collar 62 to translate collar 62 relative to post 14. Such engagement moves extension 50 between selected positions, as described herein. Actuator 80 engages end 64 causing collar 62 to translate along post 14. Translation of collar 62 causes ledge 70 to engage ledge 55 to apply a force to extension 50 such that tab 59 moves into cavity 36 to engage bone fastener 100, as described herein.

Bone fastener 100, as shown in FIGS. 7 and 8, includes a receiver 102 and a shaft 104 configured for penetrating tissue, such as, for example, vertebral tissue and/or bone. Receiver 102 is configured to receive an implant, such as, for example, a spinal rod (not shown). Receiver 102 is configured for engagement with adapter 12. Receiver 102 includes spaced arms 106, 108 defining a U-shaped channel. Arms 106, 108 include a surface 110 that defines recesses, such as, for example, slots 112 configured to engage flanges 38 of adapter 12, as described herein. In one embodiment, slots 112 are positioned at opposing sides of each arm 106, 108, as shown in FIGS. 7 and 8. Arms 106, 108 include surface 114 that defines a cavity, such as, for example, a recess 116 configured to receive tab 59 of extension 50.

In assembly, operation and use, system 10, similar to the systems and methods described herein, is employed with a surgical procedure, such as, for example, a correction treatment to treat trauma of the spine, such as, for example, thoraco-lumbar and lumbar fractures. In some embodiments, system 10 can be employed with a correction treatment for spinal disorders, such as, for example, degenerative disc disease, disc herniation, osteoporosis, spondylolisthesis, stenosis, scoliosis and other curvature abnormalities, kyphosis, tumor and fractures. In some embodiments, one or all of the components of system 10 can be delivered or utilized as a pre-assembled device or can be assembled in situ.

For example, system 10 can be employed with a surgical correction treatment of an applicable condition or injury of an affected section of a spinal column (not shown) and adjacent areas within a body, such as, for example, vertebral levels. In some embodiments, system 10 may be employed with one or a plurality of vertebrae.

In use, to treat vertebrae, a medical practitioner obtains access to a surgical site including vertebrae in any appropriate manner, such as through incision and retraction of tissues. In some embodiments, system 10 can be used in any existing surgical method or technique including open surgery, mini-open surgery, minimally invasive surgery and percutaneous surgical implantation, whereby vertebrae is accessed through a mini-incision, or sleeve that provides a protected passageway to the area. Once access to the surgical site is obtained, the particular surgical procedure can be performed for treating a spine disorder.

An incision is made in the body of a patient and a cutting instrument (not shown) creates a surgical pathway for implantation of components of system 10. A preparation instrument (not shown) can be employed to prepare tissue surfaces of vertebrae as well as for aspiration and irrigation of a surgical region.

Pilot holes are made in selected levels of vertebrae for receiving one or more bone fasteners 100. Shaft 104 of each bone fastener 100 is oriented with the bony anatomy of vertebrae and a driver (not shown) is manipulable to drive, torque, insert or otherwise fasten each bone fastener 100 with vertebrae. Each shaft 104 is threaded and engaged with tissue.

Adapter 12 is manipulated, in the direction shown by arrow A in FIG. 7, such that post 14 is engaged with arms 106, 108 of receiver 102. Flanges 38 are aligned for mating engagement with slots 112. In some embodiments, as post 14 engages receiver 102, arms 106, 108 contact limits 40, 42 such that post 14 bottoms out against bone fastener 100. Actuator 80 is mounted with surface 56 for translating collar 62.

Extension 50 is aligned with mating surface 34, as described herein, such that tab 59 is disposed in a selected position, such as, for example, a first and tab 59 is substantially aligned with mating surface 34. In some embodiments, collar 62 is disposed with post 14 such that ledge 76 is disposed with surfaces 31, 33 to prevent rotation of adapter 12 relative to bone fastener 100.

In some embodiments, a surgical tool and/or instrument (not shown) engage actuator 80. The surgical tool engages actuator 80 such that actuator 80 threadably engages surface 56 and translates relative thereto, in the direction shown by arrow B in FIG. 8. Actuator 80 abuts and engages collar 62 to translate collar 62 relative to post 14. Such engagement, as described herein, causes extension 50 to move, pivot and/or rotate about connection point 52 between a first selected position such that extension 50 is aligned with mating surface 34 and a second selected position such that extension 50 engages bone fastener 100.

Actuator 80 engages end 64 causing collar 62 to translate along post 14. Translation of collar 62 causes ledge 70 to engage ledge 55 to apply a force to extension 50 such that tab 59 is urged into cavity 36 to engage bone fastener 100, as described herein. As such, tab 59 is disposed in recess 116 such that extension 50 is locked with receiver 102 and adapter 12 captures bone fastener 100. In some embodiments, surgical instruments may be connected with adapter 12 to manipulate bone fasteners 100 and/or introduce a spinal rod into receivers 102. For example, adapter 12 can capture bone fastener 100 so that the vertebrae connected with bone fasteners 100 can be compressed and/or distracted. In some embodiments, the components of system 10 can include surgical instruments connectable to adapter 12, which compress and/or distract vertebrae connected with bone fasteners 100 to restore vertebral body height and curvature of vertebrae by rotating vertebra about a center of rotation corresponding to a bone fastener adjacent a facet joint.

Upon completion of a procedure, as described herein, the surgical instruments, assemblies and non-implanted components of system 10 are removed and the incision(s) are closed. One or more of the components of system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of rods, plates, connectors and/or bone fasteners for use with a single vertebral level or a plurality of vertebral levels.

In some embodiments, one or more of fasteners 100 may be engaged with tissue in various orientations, such as, for example, series, parallel, offset, staggered and/or alternate vertebral levels. In some embodiments, one or more of fasteners 100 may comprise MAS, sagittal angulation screws, pedicle screws, mono-axial screws, uni-planar screws, facet screws, FAS, tissue penetrating screws, conventional screws, expanding screws, wedges, anchors, buttons, dips, snaps, friction fittings, compressive fittings, expanding rivets, staples, nails, adhesives, posts, fixation plates and/or posts.

In one embodiment, system 10 includes an agent, which may be disposed, packed, coated or layered within, on or about the components and/or surfaces of system 10. In some embodiments, the agent may include bone growth promoting material, such as, for example, bone graft to enhance fixation of the components and/or surfaces of system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical connector comprising:
   a first member extending along a longitudinal axis between a first end and an opposite second end, the first end including a threaded outer surface, the second end including a locking element and a mating surface engageable with an implant, the first end being immovable relative to the second end, the second end comprising spaced apart arms defining an implant cavity therebetween, the implant cavity extending parallel to the longitudinal axis; and
   a second member comprising a first and a second end, the first end defining an opening and the first end of the first member extending through the opening such that the first end of the first member is proximal to the first end of the second member, the second member being translatable relative to the first member to urge the locking element into engagement with the implant,
wherein at least one of the members is connectable with a surgical instrument.

2. A surgical connector as recited in claim 1, wherein the mating surface and the locking element are positioned between the arms.

3. A surgical connector as recited in claim 1, wherein the arms include opposing flanges, the flanges being engageable with at least one recess of the implant.

4. A surgical connector as recited in claim 1, wherein the locking element comprises an extension configured for disposal with a cavity of the implant.

5. A surgical connector as recited in claim 1, wherein the locking element is disposable between a first position such that a locking surface is flush with the mating surface and a second position such that the locking surface extends outwardly from the mating surface to engage the implant.

6. A surgical connector as recited in claim 5, wherein the locking element is resiliently biased to the first position.

7. A surgical connector as recited in claim 5, wherein the locking element is movable from the first position to the second position as the second member translates in a first direction and moveable from the second position to the first position as the second member translates in a second direction.

8. A surgical connector as recited in claim 1, wherein the locking element comprises a surface engageable with an inner surface of the second member to move the locking element.

9. A surgical connector as recited in claim 8, wherein the inner surface includes an annular ledge.

10. A surgical connector as recited in claim 1, wherein the threaded outer surface is configured to engage an actuator such that the actuator drives the second member relative to the first member.

11. A surgical connector as recited in claim 1, wherein the second member comprises a sleeve.

12. A surgical connector as recited in claim 1, wherein the implant comprises a screw including a receiver having spaced arms.

13. A surgical connector as recited in claim 1, wherein the first end is monolithically formed with the second end.

14. A surgical connector as recited in claim 1, wherein the implant cavity extends along a cavity axis, the cavity axis being offset from the longitudinal axis.

15. A surgical adapter comprising:
a post extending along a longitudinal axis between a first end and an opposite second end, the first end including a threaded outer surface, the second end including a locking element and a mating surface engageable with a bone fastener, the first end being immovable relative to the second end, the second end comprising spaced apart arms defining an implant cavity therebetween, the arms and the implant cavity each extending parallel to the longitudinal axis;
a collar comprising a first end and a second end, the first end defining an opening, the threaded outer surface extending through the opening such that the first end of the post is proximal to the first end of the collar; and
an actuator disposed with the first end and engageable with the collar to translate the collar relative to the post to move the locking element between a first position such that the locking element is flush with the mating surface and a second position such that the locking element extends outwardly from the mating surface to engage the bone fastener.

16. A surgical adapter as recited in claim 15, wherein the locking element is resiliently biased to the first position.

17. A surgical adapter as recited in claim 15, wherein the locking element comprises a surface engageable with an inner surface of the collar to move the locking element.

18. A surgical adapter as recited in claim 17, wherein the inner surface includes an annular ledge.

19. A surgical adapter as recited in claim 15, wherein inner surfaces of the arms are continuous with the mating surface comprises spaced arms.

20. A surgical adapter as recited in claim 15, wherein the locking element comprises an extension configured for disposal with a cavity of the bone fastener.

* * * * *